US011173018B1

(12) United States Patent
O'Beirne

(10) Patent No.: US 11,173,018 B1
(45) Date of Patent: Nov. 16, 2021

(54) ORAL HYGIENE DEVICE

(71) Applicant: Able Biomedical Devices, LLC, Seattle, WA (US)

(72) Inventor: Gerrarda O'Beirne, Seattle, WA (US)

(73) Assignee: ABLE BIOMEDICAL DEVICES, LLC, Seattle, WA (US)

(*) Notice: Subject to any disclaimer, the term of this patent is extended or adjusted under 35 U.S.C. 154(b) by 0 days.

(21) Appl. No.: 15/130,774

(22) Filed: Apr. 15, 2016

Related U.S. Application Data

(60) Provisional application No. 62/148,512, filed on Apr. 16, 2015.

(51) Int. Cl.
| | |
|---|---|
| *A61C 15/02* | (2006.01) |
| *A61C 17/22* | (2006.01) |
| *A61C 19/06* | (2006.01) |
| *A61B 1/247* | (2006.01) |
| *A61C 19/04* | (2006.01) |

(52) U.S. Cl.
CPC ............. *A61C 15/02* (2013.01); *A61B 1/247* (2013.01); *A61C 17/224* (2013.01); *A61C 19/04* (2013.01); *A61C 19/063* (2013.01)

(58) Field of Classification Search
CPC ......... A61C 15/02; A61C 15/00; A61C 17/20; A61C 17/00; A61C 17/16; A61C 17/32; A61C 17/34; A61C 17/40; A61C 17/222; A61C 3/06; A61C 3/03; A61C 5/85
USPC .......... 433/118, 119, 29, 141, 142, 143, 166
See application file for complete search history.

(56) References Cited

U.S. PATENT DOCUMENTS

| | | | | |
|---|---|---|---|---|
| 1,746,591 A | * | 2/1930 | Heymann | A61C 15/02 |
| | | | | 132/329 |
| 4,576,190 A | * | 3/1986 | Youssef | A61C 15/02 |
| | | | | 132/322 |
| 5,049,070 A | | 9/1991 | Ademovic | |
| 5,052,924 A | | 10/1991 | Berg | |
| 5,119,803 A | * | 6/1992 | Fishman | A61C 19/063 |
| | | | | 433/80 |
| 5,236,358 A | * | 8/1993 | Sieffert | A61C 17/20 |
| | | | | 433/102 |
| 5,634,790 A | * | 6/1997 | Pathmanabhan | A61B 1/00087 |
| | | | | 433/29 |
| 5,655,906 A | * | 8/1997 | Coss | A61C 17/20 |
| | | | | 433/115 |

(Continued)

FOREIGN PATENT DOCUMENTS

| | | | |
|---|---|---|---|
| DE | 4309078 | * | 9/1994 |
| EP | 1743593 B1 | | 12/2008 |

(Continued)

*Primary Examiner* — Cris L. Rodriguez
*Assistant Examiner* — Brianne E Kalach
(74) *Attorney, Agent, or Firm* — K&L Gates LLP

(57) ABSTRACT

Systems and methods are generally described for an oral hygiene device. The oral hygiene device may include a handle portion and a head portion coupled to the handle portion and including a pick head interface. A pick head may be removably coupled to the pick head interface. The pick head may include a pointed pick member. An image capture device may be disposed in the head portion. The image capture device may be effective to capture image data representing images of an area proximal to a tip of the pointed pick member. A vibration element may be coupled to the pick head interface. The vibration element may be effective to vibrate the pick head.

32 Claims, 13 Drawing Sheets

(56) References Cited

U.S. PATENT DOCUMENTS

| | | | |
|---|---|---|---|
| 5,730,594 A | 3/1998 | Sharp | |
| 5,743,731 A * | 4/1998 | Lares | A61B 1/00087 |
| | | | 433/29 |
| 5,810,587 A * | 9/1998 | Bruns | A61C 3/025 |
| | | | 424/49 |
| 5,893,715 A * | 4/1999 | Boland | A61C 17/16 |
| | | | 433/118 |
| 5,924,864 A * | 7/1999 | Loge | A61B 17/1622 |
| | | | 433/112 |
| 6,190,167 B1 | 2/2001 | Sharp | |
| 6,447,293 B1 * | 9/2002 | Sokol | A61C 15/047 |
| | | | 132/322 |
| 6,491,520 B1 * | 12/2002 | Carlsson | A61C 3/02 |
| | | | 433/118 |
| 6,517,348 B1 | 2/2003 | Ram | |
| 6,726,531 B1 * | 4/2004 | Harrel | A61C 3/03 |
| | | | 433/119 |
| 6,953,341 B2 | 10/2005 | Black | |
| D520,683 S | 5/2006 | Kling | |
| 7,261,561 B2 | 8/2007 | Ruddell et al. | |
| 8,938,838 B2 | 1/2015 | Vashi | |
| 2001/0034006 A1 * | 10/2001 | Lang | A61C 15/047 |
| | | | 433/118 |
| 2005/0244788 A1 * | 11/2005 | Feine | A61C 3/03 |
| | | | 433/165 |
| 2006/0174910 A1 * | 8/2006 | Coopersmith | A61C 17/16 |
| | | | 132/321 |
| 2007/0093725 A1 * | 4/2007 | Shaw | A61B 5/097 |
| | | | 600/543 |
| 2007/0190485 A1 * | 8/2007 | Hayman | A61C 1/07 |
| | | | 433/118 |
| 2007/0259307 A1 * | 11/2007 | Quan | A61C 3/00 |
| | | | 433/25 |
| 2009/0176185 A1 | 7/2009 | Chen | |
| 2010/0229887 A1 * | 9/2010 | Pfenniger | A46B 3/18 |
| | | | 132/321 |
| 2011/0065063 A1 * | 3/2011 | Bock | A61C 1/14 |
| | | | 433/118 |
| 2013/0061412 A1 | 3/2013 | Vashi | |
| 2013/0209374 A1 * | 8/2013 | Castellana | A61K 8/99 |
| | | | 424/48 |
| 2015/0142621 A1 * | 5/2015 | Gray | G06Q 10/087 |
| | | | 705/28 |
| 2015/0238294 A1 * | 8/2015 | Coopersmith | A61C 15/02 |
| | | | 132/329 |

FOREIGN PATENT DOCUMENTS

| | | | |
|---|---|---|---|
| EP | 1858432 B1 | | 6/2012 |
| EP | 2976966 | * | 1/2016 |
| WO | WO2008060482 | * | 5/2008 |

\* cited by examiner

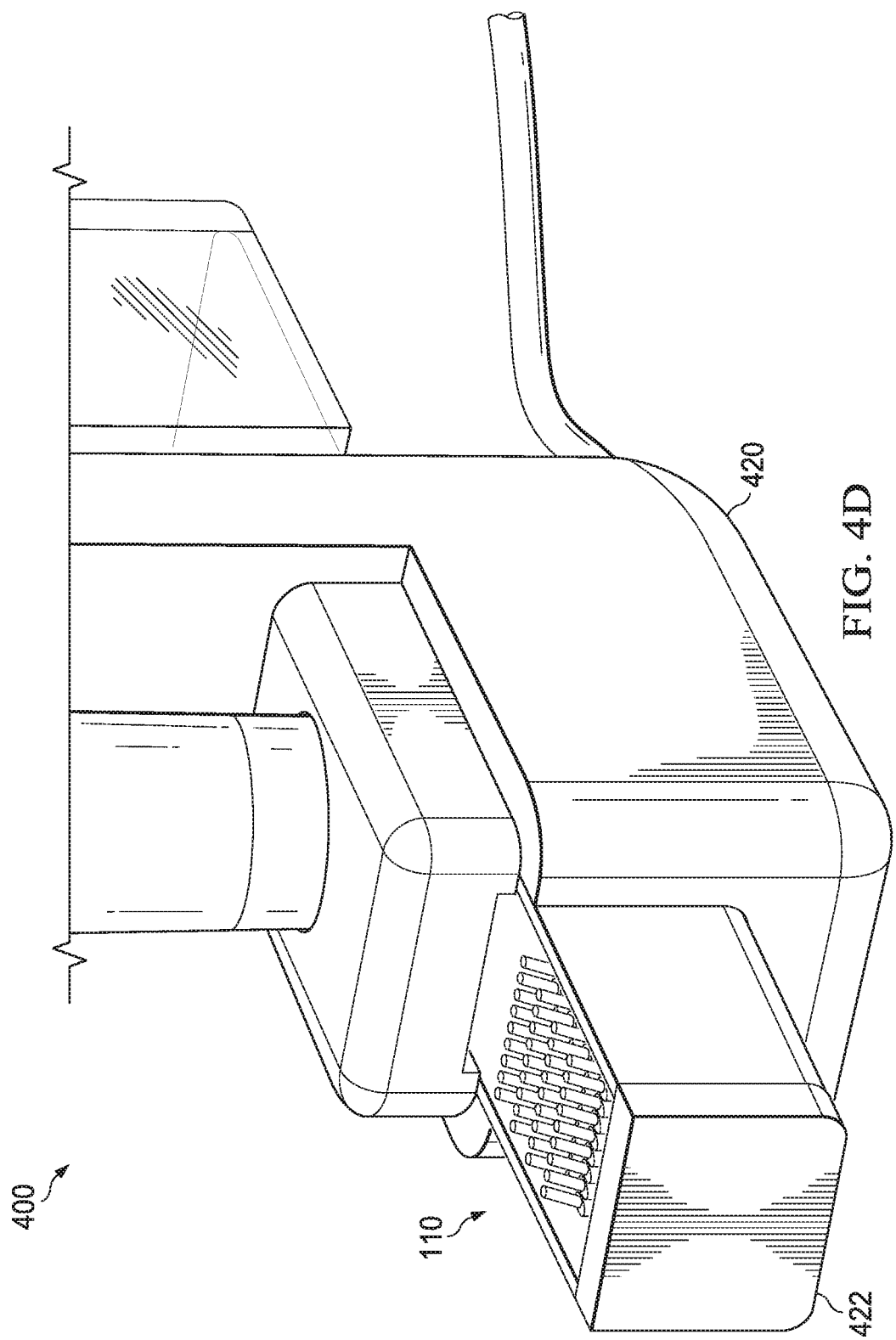

ORAL HYGIENE DEVICE

CROSS-REFERENCE TO RELATED APPLICATIONS

This application claims the benefit of U.S. Provisional Application No. 62/148,512, filed Apr. 16, 2015, the disclosure of which is incorporated herein by reference in its entirety.

FIELD

This application relates to oral hygiene devices.

BACKGROUND

Dental plaque is a biofilm that forms around teeth and gums. It is composed of many groups of organisms embedded in a sticky matrix. If it is not removed on a regular basis it can give contribute to the development of dental cavities and gum disease. Gum disease is highly prevalent in the United States population. Findings based on data collected as part of the Center for Disease Control's 2009-2012 National Health and Nutrition Examination Survey (NHANES), designed to assess the health and nutritional status of adults and children in the United States, estimated that 46%, or 64.7 million American adults aged 30 years and older, have mild, moderate or severe periodontitis. Gingivitis is the earliest stage of gum disease. If this is left untreated it can progress to the more serious form called periodontitis where there is damage to the tooth support and possibly tooth loss. Oral disease may also be linked to conditions elsewhere in the body such as heart disease, stroke, diabetes, arthritis and adverse pregnancy outcomes. Commercially available oral hygiene devices may be ineffective at reaching and removing plaque buildup along and below the gum margin.

Accordingly, there is a need for improved oral hygiene devices and methods.

BRIEF DESCRIPTION OF DRAWINGS

FIG. 4D illustrates an enlarged view of a pick storage compartment in an oral hygiene system, in accordance with various aspects of the present disclosure.

DETAILED DESCRIPTION

Plaque is an oral biofilm that has a causative role in the development of caries and periodontal disease. It is composed of structured layers of bacterial colonies and other micro-organisms embedded in a polysaccharide matrix. By nature, it is a sticky, tenacious film that can attach to all surfaces of the tooth, root, dental implant, braces, or oral appliances. It is easily removed in the early stages of formation. If it is allowed to remain for a period of time, components can start to mineralize, and, as a consequence, professional care is required for its removal. Described herein are embodiments that circumferentially access all areas, most importantly the space between the gum and the tooth, root or implant, etc., to gently but firmly remove the biofilm. Removal of the biofilm on a regular basis aborts the cycle of destruction caused by the presence of micro-organisms that have been implicated in the development of caries and periodontal disease.

Figure 1A:
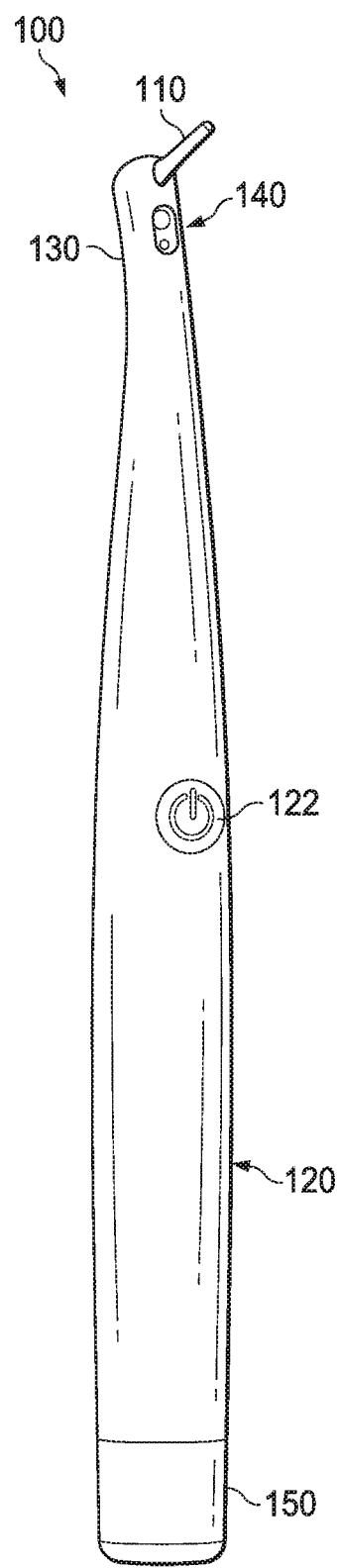
FIG. 1A illustrates an angled view of an oral hygiene device, in accordance with various aspects of the present disclosure.
Figure 1B:
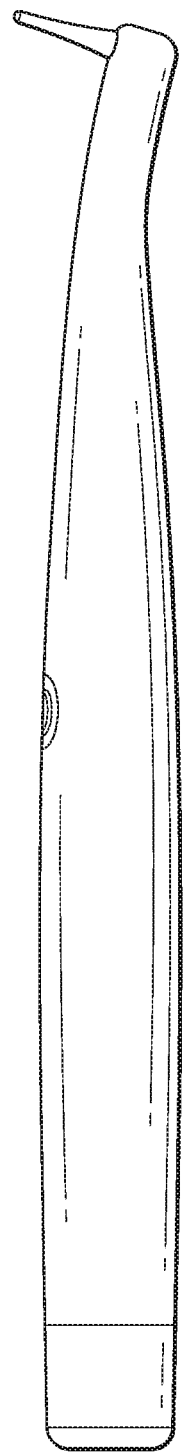
FIG. 1B illustrates a side view of the oral hygiene device of FIG. 1A, in accordance with various aspects of the present disclosure.
Figure 1C:
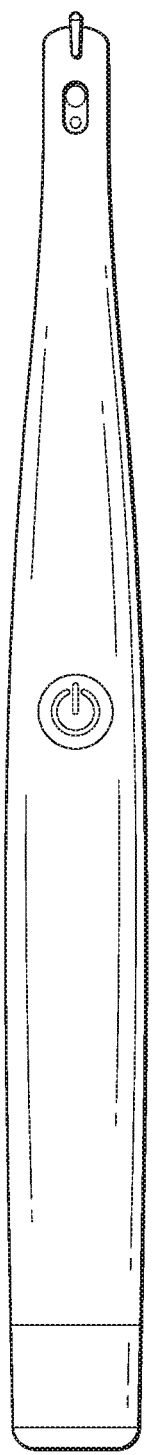
FIG. 1C illustrates a front view of the oral hygiene device of FIGS. 1A and 1B, in accordance with various aspects of the present disclosure.
Figure 1D:
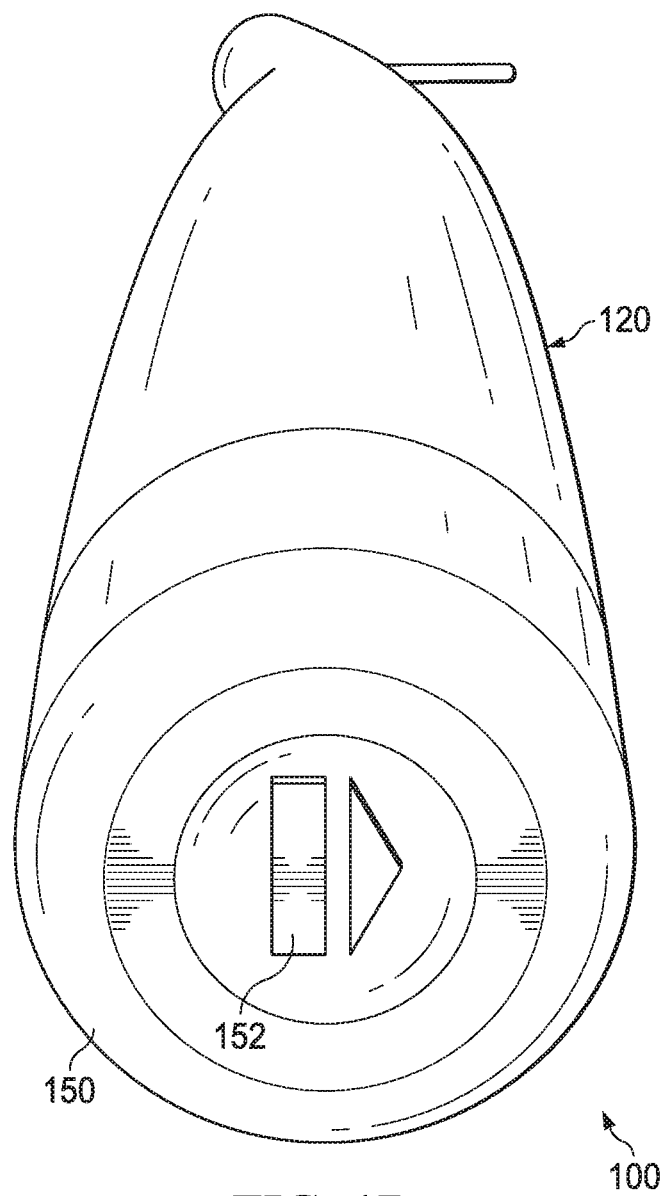
FIG. 1D illustrates a perspective view of the bottom of the oral hygiene device of FIGS. 1A-1C, in accordance with various aspects of the present disclosure.

FIGS. 1A-1D illustrate various views of an oral hygiene device 100, in accordance with embodiments of the present invention. FIG. 1A shows an angled view of the device 100, FIG. 1B shows a side view of the device 100, FIG. 1C shows a front view of the device 100, and FIG. 1D shows a perspective view of the bottom of the device 100. The oral hygiene device 100 is a powered toothpick handset utilizing sonic vibration of a replaceable pointed pick head 110. The device 100 includes a handle portion 120 which is gripped by the user when utilizing the device. A head portion 130 is provided at a distal end of the device 100 and an inductive charging portion 150 is provided at a proximal end of the device 100. The dimensions of the device 100 may vary, but in one embodiment, the device 100 is approximately 140 mm tall, 12 mm wide at the inductive charging portion 150, 5 mm wide at the head portion 130, and the pick head 110 is 10 mm long.

The head portion 130 includes a pick head interface 135 for coupling with the pick head 110. The pick head interface 135 securely holds the pick head 110 in place while the user is operating the device 100. The pick head 110 includes a pointed pick member 111, which may comprise any material suitable for use in cleaning teeth and gums. In some embodiments, the pick head 110 is made of wood, cellulose, or a biodegradable material, or may be made of nylon, plastic, or other synthetic material such as silicone. It may be desirable for the pick head 110 to be made of a pliable material, so as to avoid damage to the teeth or gums if the user applies an excessive pressure during use. It may also be desirable for the pick head 110 to have a porous or coarse surface to improve the pick head 110's ability to remove food particles and plaque from a subject's teeth. In some embodiments, it is desirable for the pick head 110 to include a firm core and softer outer region surrounding the core, so that the pick head 110 may engage the contours of the user's teeth. In particular, tooth implants may have "wine glass" shaped curvature wherein a larger crown overlies a smaller root portion of the implanted tooth. Soft outer regions of pick head 110 may be particularly well-suited for conforming to the curvature beneath the crown of an implanted tooth. Additionally, a soft outer region of pick head 110 may allow for pick head 110 and/or pick member 111 to more easily clean between teeth, and clean irregular surfaces and/or pockets found on a user's teeth.

In some examples, the outer surface of pick head 110 may be softer than an average material hardness of dentin or roots of human or animal teeth. In various examples the pick head 110 may be softer than 3 Mohs on the Mohs hardness scale, or 70 HK using the Knoop hardness test. As will be discussed in further detail below, in some examples, pick head 110 may have visual reference markings, which may be used in conjunction with data recorded by an integrated digital camera module to determine various characteristics such as the relative position of the pick head 110 in a user's mouth or the depth of a pocket found in the user's teeth.

Unlike standard toothpicks, which are typically used for cleaning between teeth, the pick head 110 may be guided circumferentially around the user's teeth and gums. It may also be desirable for the pick member to be impregnated with, coated with, and/or able to dispense a treatment to further enhance biofilm removal. Examples of such treatment may include hydrogen peroxide, xylitol, fluoride, ginger, pineapple, cranberry, sodium hypochlorite, sodium chlorate, chlorine dioxide, chlorhexidine, essential oils, such as spearmint oil or tea tree oil, and other antibacterial and/or antiseptic agents. In some other examples, the treatments may include probiotics for promoting growth and cultivation of a desired biome. In some further examples, treatments may include molecules which may be effective to block certain bacterial functions, such as the ability of bacteria to adhere to one another and/or to the surface of teeth or gums. Adhesion of bacteria to each other and to host surfaces is a prerequisite to the development and proliferation of biofilm. For example, Strep Mutans is a pathogen which exhibits a surface antigen allowing it to bind to salivary proteins on the tooth surface. Treatments may include antibodies which block these antigens, preventing attachment and proliferation on the tooth. In another example, host-receptor assemblies used for bacterial attachment may be disrupted via treatments. For example, depletion of host glycosphingolipids (GSLs) through enzyme treatments may slow and prevent bacterial attachment. In another example, a treatment may include non-pathogenic organisms which compete with pathogenic organisms for attachment proteins on the tooth surface, thereby slowing and helping to prevent attachment and proliferation of pathogenic biofilms.

In some other examples, treatments may include molecules which down-regulate the destructive inflammatory response in teeth or gums, such as molecules which block parts of the Complement Cascade. The Complement System is a part of the hosts' defense system that enhances the immune response to clear the body of pathogens. It plays a central role in regulation of the hosts' inflammatory response to a microbial challenge. *Porphyromonas gingivalis* is considered a key periodontopathogen. Despite being present in low numbers, it can greatly manipulate and promote the virulence of biofilm. It appears to have the ability to hijack the complement system to benefit its own survival via influencing the action of the complement component C5a and its receptor C5aR with the side effect of causing structural breakdown of the periodontal tissues. Local administration of an antagonist to C5aR (PMX-53) could potentially negate this key role of *Porphyromonas gingivalis* and limit or eliminate the collateral periodontal destruction.

Additionally, in some examples, pick head 110 may be used to collect microbial and/or fluid samples, such as gingival crevicular fluid, from the user's mouth. Samples may be deposited in a sterile container for subsequent analysis. For example, user may scrape pick head 110 along an interior surface of the sterile container in order to deposit a sample collected from the user's mouth within the sterile container. The sterile container may thereafter be sealed and sent to a lab or dental practitioner for detailed analysis. In some examples, the sterile container may be a mailer, such as a sterile, sealable polypropylene or polystyrene pouch, envelope, or tube that is pre-addressed to a particular lab, researcher, archive, dental practitioner and/or other dental professional or dental assistant.

In some embodiments, the pick head 110 is intended for single use and should be detached from the device 100 and disposed of after each use. In other embodiments, the pick head 110 may be sufficiently durable as to be used for multiple cleaning sessions.

The device 100 includes a rechargeable battery and charger circuitry. The battery may be recharged through an electrical connector or via a wireless charging interface (e.g., the inductive charging portion 150). The inductive charging portion 150 includes a secondary coil for coupling with an electromagnetic field generated by a primary coil in the charger base 410 (shown in FIG. 4), similar to the way in which conventional electric toothbrushes are charged.

A power button 122 in the handle portion 120 may be configured to illuminate in different colors or patterns to provide status information to the user. For example, the button 122 may illuminate red and/or may flash to indicate that the battery is low, and may illuminate green when the device 100 is powered on for use.

As seen in FIG. 1D, the bottom of the device 100 may include an eject button 152, which, when depressed by the user, ejects the pick head 110 from the pick head interface 135. In some examples, pick head interface 135 may be a press-fit connection which is effective to securely hold pick head 110 to device 100. Depressing eject button 152 may cause a release mechanism to produce a force along the axis of pick head 110 (e.g., along the long axis of pick head 110 which extends along pick head 110 from device 100 to the exposed tip of pick member 111), the force being directed away from device 100 along the axis of pick head 110, such that the force decouples pick head 110 from pick head interface 135. In some examples, depressing eject button 152 may cause a dilation of an enclosure which at least partially surrounds and securely holds a portion of pick head 110 inside of device 100. Dilation of the enclosure may allow for pick head 110 to be easily removed from device 100. In some examples, when the enclosure is dilated by depressing eject button 152, orienting device 100 in such a way that the long axis of pick head 110 faces downward, may allow pick head 110 to be removed by the force of gravity without requiring a user to apply a pulling force to pick head 110. In another example, when the enclosure is dilated by depressing eject button 152, a mechanism such as a piston, flexible diaphragm, or other structure disposed within device 100 and coupled to eject button 152 may apply a force to the portion of pick head 110 which is disposed inside of device 100. Such a force may be directed away from device 100 along the axis of pick head 110, and may eject pick head 110 from device 100 while the enclosure is dilated as a result of the depression of eject button 152. Embodiments described above where the pick head 110 may be removed without requiring a user to touch the pick head 110 may be advantageous, particularly in examples where the pick head is to be sent for microbial or fluid analysis, where human handling of the pick head may otherwise contaminate the collected sample.

The portion of pick head 110 which is disposed inside of device 110 and which engages with pick head interface 135 may have one or more flanges and/or recessed portions which may securely engage with the enclosure of pick head interface 135, described above. In some other examples, pick head interface 135 may include a magnet which is effective to securely hold pick head 110 to device 100 in conjunction with the size and shape of the portion of pick head 110 which fits into device 100, and the size and shape of the portion of pick head interface 135 which is configured to receive pick head 110. In examples where pick head interface 135 includes a magnet, pick head 110 may comprise a ferrous material positioned adjacent to the pick head interface 135 when the pick head 110 is engaged with the pick head interface 135.

Figure 2A:
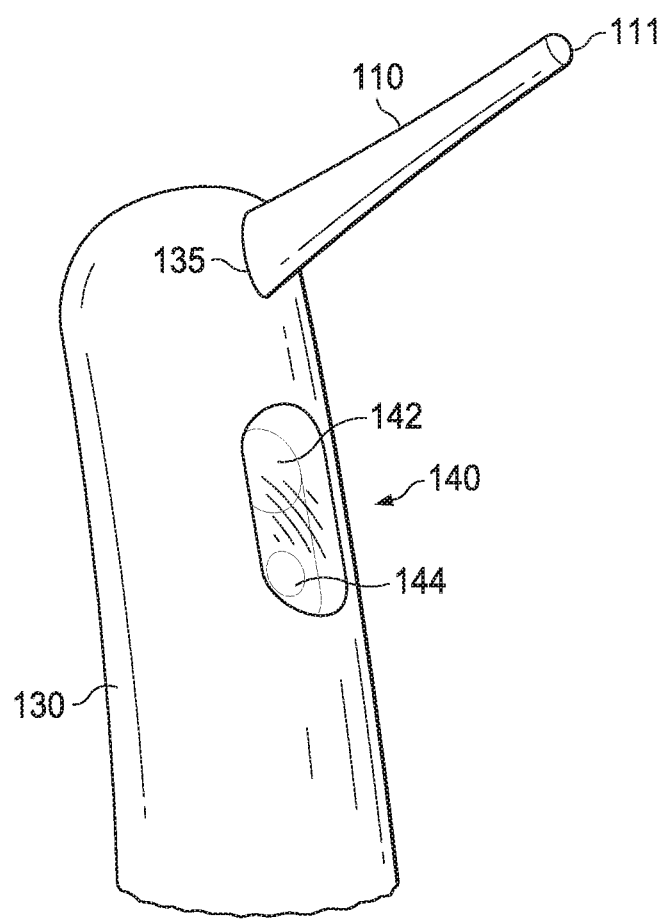
FIG. 2A illustrates an enlarged view of a head portion of an oral hygiene device, in accordance with various aspects of the present disclosure.

FIG. 2A is an enlarged view of the head portion 130. In some embodiments, the device 100 includes an image capture device 140 for capturing images of area surrounding the pick head 110, such as portions of the user's mouth, teeth, and gums during operation of the device 100. The image capture device 140 includes a lens 142 for a digital camera module contained within the device 100, and a light source 144 (e.g., an LED light) for illuminating the area to be imaged. The image capture device 140 may capture still images or video of the area surrounding the pick head 110, and may store this data in a memory (e.g., located inside of device 100) for later analysis and/or transmission to a memory in charger base 410 or other computing device, or may transmit the images and/or video in real-time over a wide area network (WAN) to another computing device, such as a computer operated by the user's health care provider. The light source 144 may comprise a white LED, or may produce a different color to accentuate the features being observed. For example, the light source 144 may generate ultraviolet light, which may be used in conjunction with fluorescent markers, stains, and/or other plaque-disclosing tablets. In some other examples, head portion 130 and/or device 100, more generally, may include a light source 144 without a camera module or other imaging sensor to allow for illumination of a user or subject's mouth without capturing images.

Figure 2B:
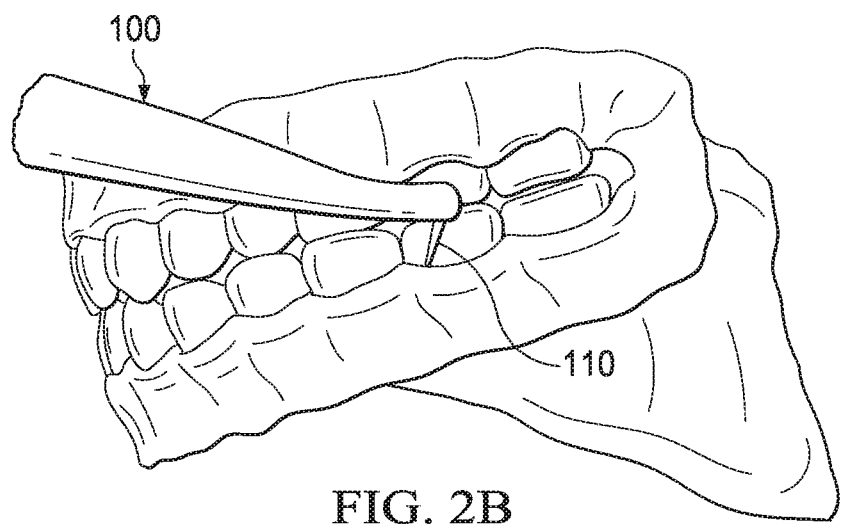
FIG. 2B depicts an image of an oral hygiene device being used to clean teeth in a user's mouth, in accordance with various aspects of the present disclosure.

FIG. 2B illustrates an image of device 100 being used to clean teeth in a user's mouth, in accordance with various aspects of the present disclosure. As shown, pick head 110, including pick member 111, may be guided along user's teeth, slightly beneath the gum line of user's teeth, between user's teeth, and/or within pockets or furcations on user's teeth during a cleaning session.

Figure 3:
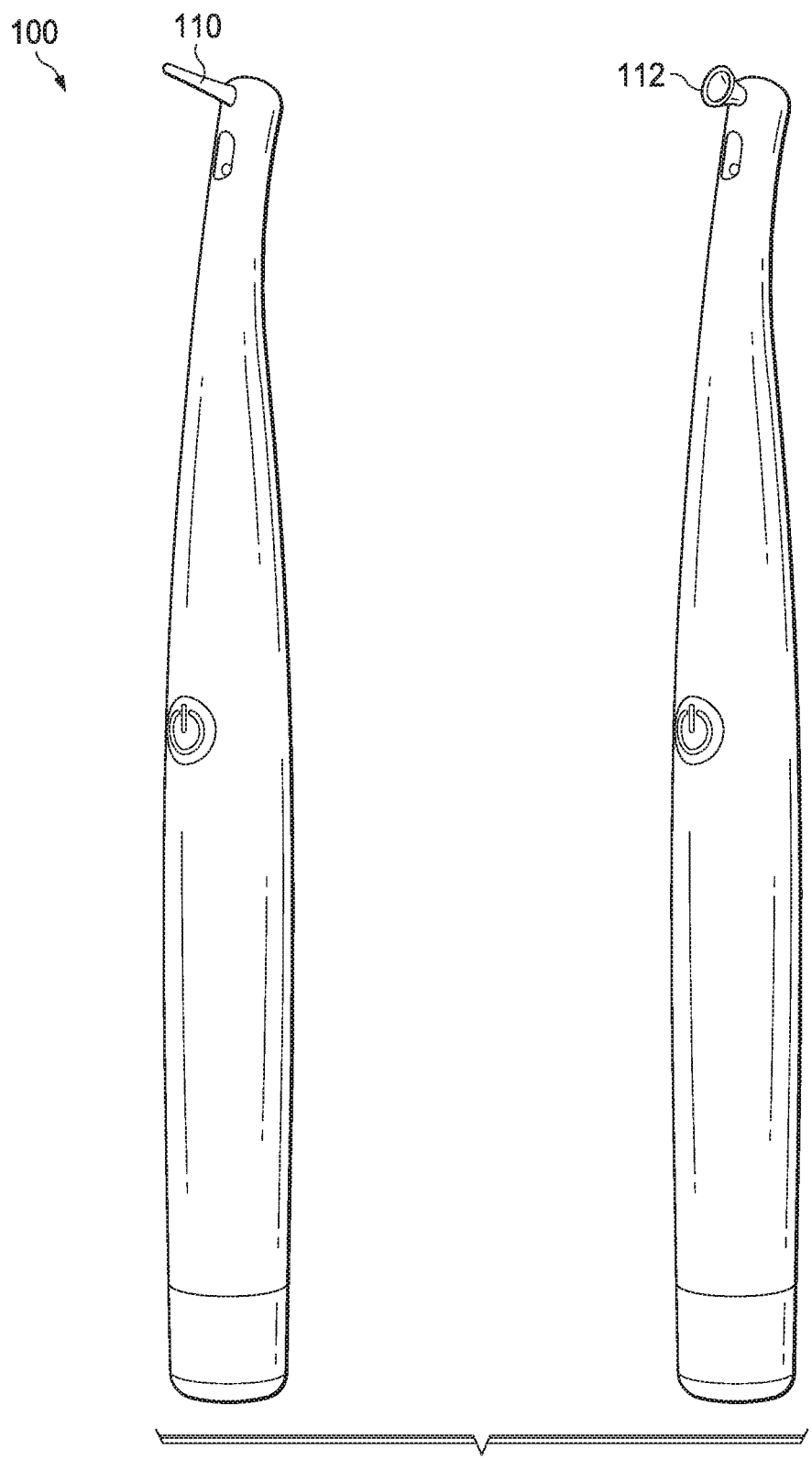
FIG. 3 illustrates alternative replacement heads for an oral hygiene device, in accordance with various aspects of the present disclosure.

FIG. 3 illustrates alternative replacement heads for the device 100. In FIG. 3, the pick head 110 can be detached and replaced with a pick head 112. The pick head 112 may be a polisher head, and may comprise, for example, a polishing cup similar to the polishing cups used with rotary polishing tools by dentists. As will be discussed in further detail below, pick head 110 and/or pick head 112 may be coupled to a vibrating element effective to vibrate pick head 110 and/or pick head 112. Pick head 112 may include one or more filaments, flanges, textured bumps, raised ridges, circles, spirals, bristles, or other textured features to aid in the removal of biofilm and/or food particles from a user's teeth during operation of device 100.

FIGS. 4A-4D illustrate an oral hygiene system 400 including a device 100 and a charging base 410. The charging base 410 may include a stand portion 420, a cover 430, and a power cord 440. Power cord 440 may be effective to supply alternating current to charging base 410 and to charging circuitry of charging base 410. The stand portion 410 may include the primary coil and ferrous core for recharging the device 100, and a rear support 414 having a support platform 416 (shown in FIG. 4C) for supporting the cover 430.

Figure 4A:
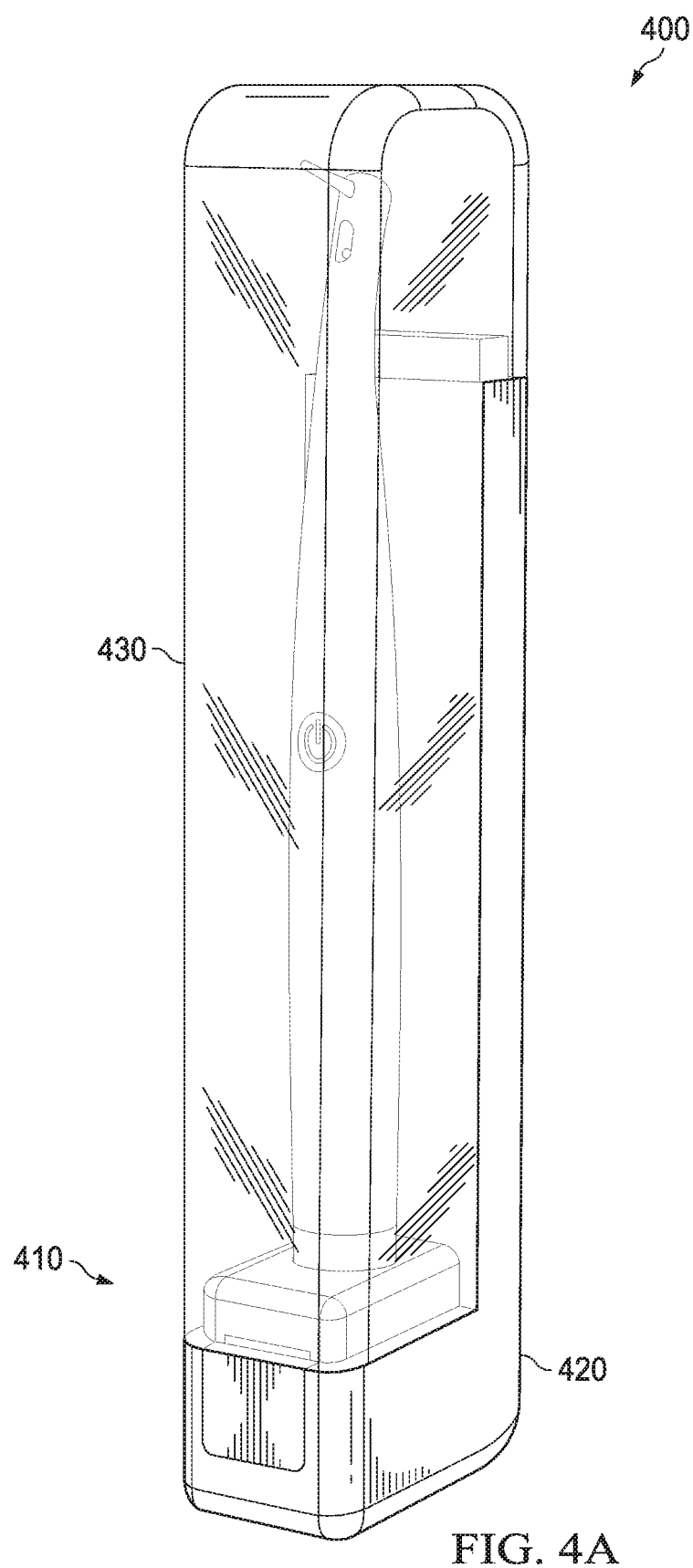
FIG. 4A illustrates a cover of a charging base for an oral hygiene device, in accordance with various aspects of the present disclosure.

FIG. 4A shows the cover 430 in the closed configuration, such that it covers the device 100. This improves the aesthetic appearance of the system 400 and reduces the amount of environmental contaminants which may be deposited on the pick head 110. The cover 430 may have any desired aesthetic appearance, and could be opaque or translucent.

Figure 4B:
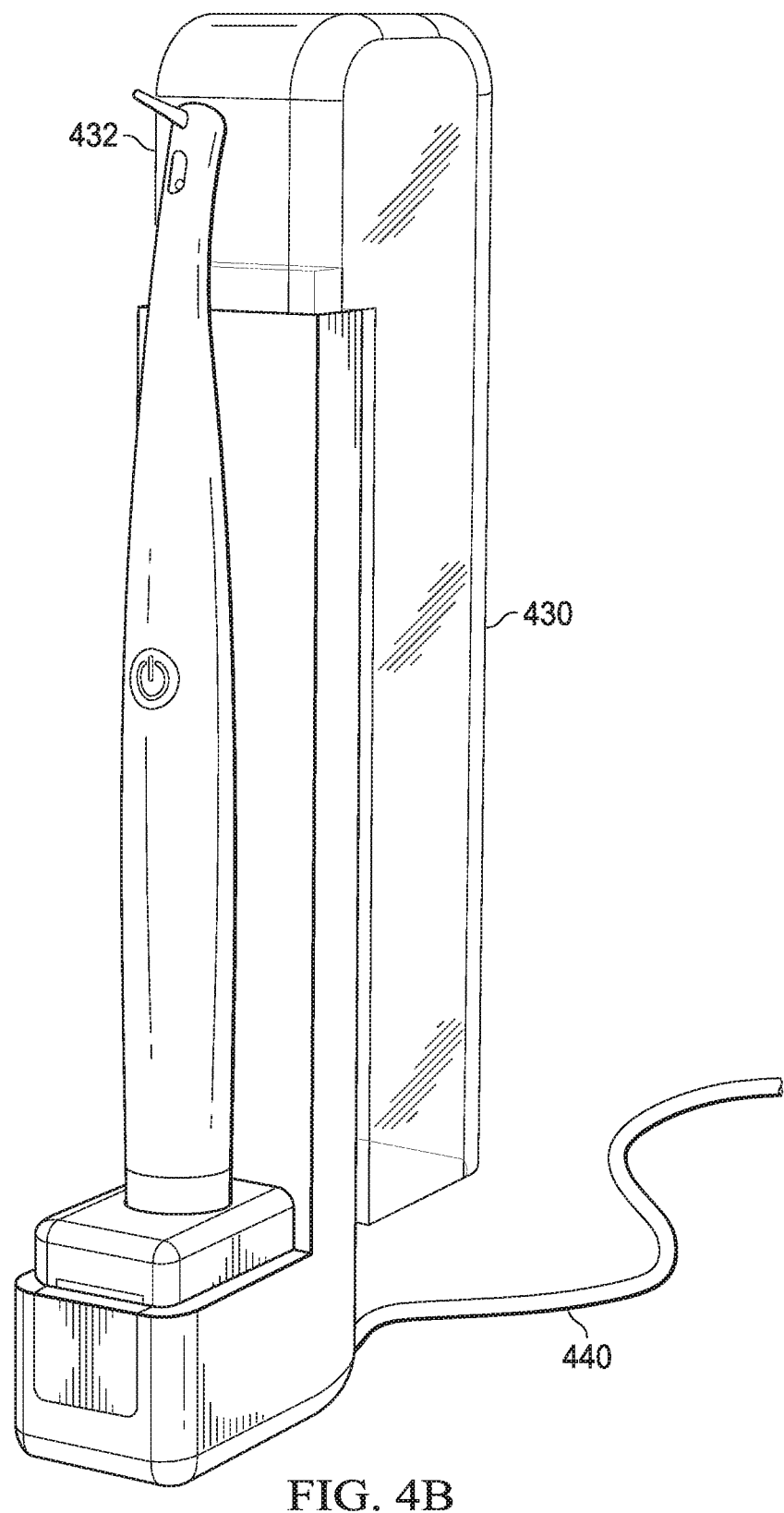
FIG. 4B illustrates the cover of FIG. 4A in an open configuration, in accordance with various aspects of the present disclosure.
Figure 4C:
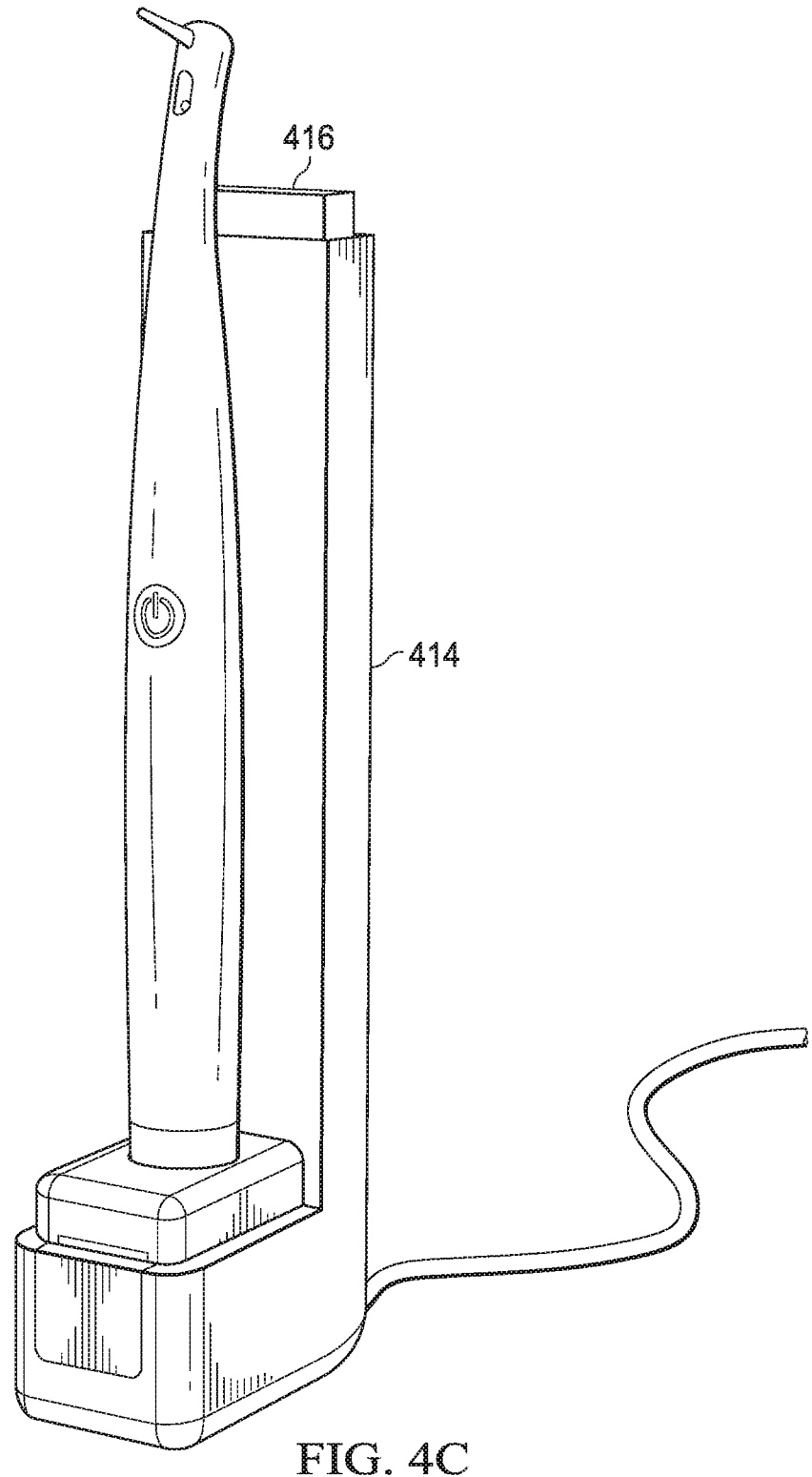
FIG. 4C depicts a rear support and a support platform for an oral hygiene system, in accordance with various aspects of the present disclosure.

FIG. 4B shows the cover 430 in the open configuration, such that the device 100 is accessible for use. In the illustrated embodiment, the cover 430 includes an overhang portion 432, which is supported by the support platform 416 in either the closed configuration shown in FIG. 4A or the open configuration shown in FIG. 4B. The arrangement provides a convenient place to store the cover 430 when the device 100 is in use. FIG. 4C shows the system 400 with the cover 430 removed. FIG. 4C depicts a rear support 414 having a support platform 416 for supporting the cover 430 (shown in FIG. 4A).

FIG. 4D is an enlarged view showing a pick storage compartment 422 in the stand portion 420 of the system 400. Stand portion 420 of charging base 410 may be sized and shaped so as to physically couple with handset device 100. As will be described in further detail below, a primary coil of an inductive charging circuit disposed in charging base 410 may be configured to electrically couple with a secondary coil in device 100 to charge a rechargeable battery of device 100. This pick storage compartment 422 may be used to store a plurality of replacement pick heads 110. Although a drawer is depicted in FIG. 4D, in some examples pick storage compartment 422 may instead be a small cabinet, recessed space, tube, or series of slots or other openings in which to hold one or more replacement picks. In some examples, a compact form factor may be of great importance to a particular design of device 100 and system 400. In such examples, device 100, charging base 410, and pick storage compartment 422 may be designed with portability and mobility in mind, so that the form factors remain as small as possible without impacting the function of the various components of device 100 and system 400. In some examples, a sensor may be configured to be in communication with pick storage compartment 422. For example, a piezoelectric sensor, for sensing pressure produced by replacement pick heads 110 in pick storage compartment 422, or an optical sensor, such as an infra-red sensor, may be effective to determine that fewer than a certain number of replacement pick heads 110 remain in pick storage compartment 422. In some examples, device 100 may produce an indicator, such as a warning light, audible tone, displayed message or other perceivable indicator, in response to the determination that fewer than a certain number of replacement pick heads 110 remain in pick storage compartment 422. In some implementations, such a sensor may be effective to send a signal to a processor in communication with device 100. The processor, in response to the signal, may re-order replacement pick heads 110 through, for example, an e-commerce website chosen by a user of device 100. In various examples, a user may configure automatic-reordering of replacement pick heads 110 as described above through an interface of a mobile application associated with device 100. Automatic reordering may be an optional feature and may be selectively disabled by the user.

Figure 6A:
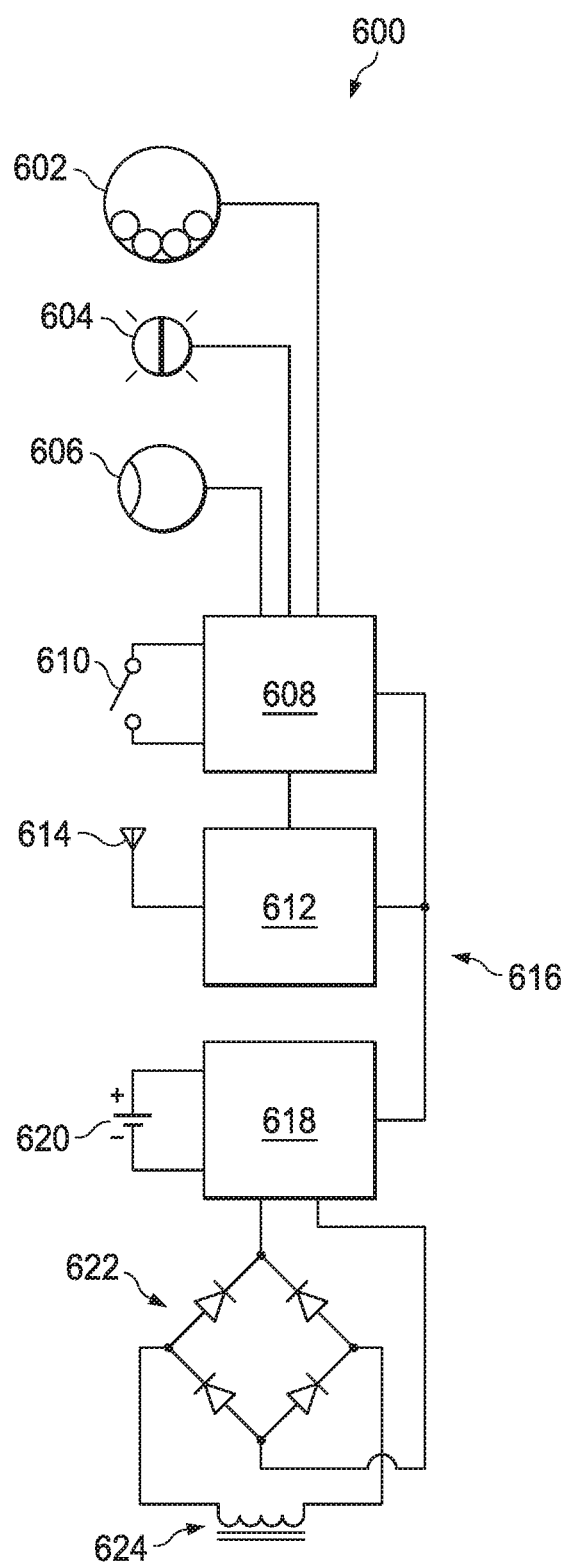
FIG. 6A illustrates a block diagram showing an examples of a vibration motor implementation of an oral hygiene device using a vibration element, in accordance with various aspects of the present disclosure.

The device 100 includes a rechargeable battery, a control module, and a vibration element. The vibration element is coupled to the pick head 110 via the pick head interface 135 for vibrating the pick head 110. In some embodiments, the vibration element may comprise a motor having an eccentric weight, which when rotated causes the pick head 110 to vibrate at the desired frequency. FIG. 6A is a simplified block diagram illustrating an example of a vibration motor implementation of device 600 utilizing such a vibration element. In FIG. 6A, the device 600 includes a microcontroller 608 operatively coupled to control a vibrator motor 602, a light source 604, and an imaging device 606. A switch 610 can be actuated by a user to begin a cleaning session. The microcontroller 608 is coupled to a wireless communications radio 612 (e.g., a Wi-Fi or Bluetooth radio) and an antenna 614. The device 600 further includes a charging circuit 618 coupled to a battery 620 and an inductive charging component 622, which includes a wireless charging coil 624 for inductive coupling with a charging coil in the charging base 410. A power bus 616 distributes power to the various components of the device 600.

Figure 6B:
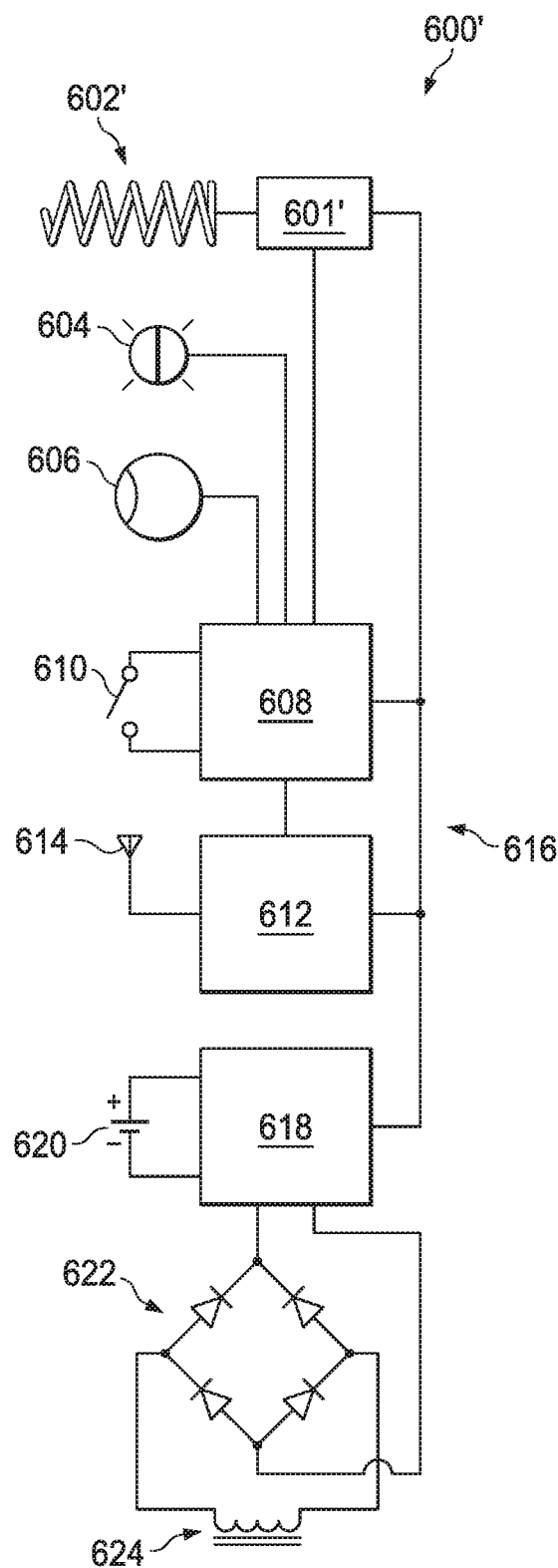
FIG. 6B illustrates an oral hygiene device including a vibration element with a resonant linear actuator and a controller, in accordance with various aspects of the present disclosure.

FIG. 6B illustrates an alternative embodiment of a device 600' in which the vibration element comprises a resonant linear actuator 602' and controller 601' which operates at the mechanism's resonant frequency. Unlike a vibration motor, the amplitude of vibration in the linear resonant actuator implementation may be controlled independent of frequency. In yet other embodiments, the vibration element may comprise a piezoelectric bending actuator coupled to the pick head 110. Many conventional piezoelectric devices provide only small displacements, so mechanical advantage may be used to increase the stroke of the pick head movement. In other embodiments, the vibration element may be implemented using solenoid, electro-magnetics, acoustic, mechanical, or microelectrical-mechanical systems (MEMS).

The vibration element may produce vibrations in the desired frequencies, such as, for example, between about 20 Hz to about 2,000 Hz, or, more preferably, less than 1,000 Hz. The vibrations may be, e.g., sonic or ultrasonic. In some embodiments, the pick head 110 provides operating strokes of 31,000 per minute or at an audible range of approximately 20,000 Hz. In some examples, vibrations which are in the sonic range may provide an audible indication to the user that device 100 is working properly and therefore serve as encouragement for a user to regularly use device 100.

The pick head 110 is mechanically coupled to the vibration element. This can be accomplished using any variety of mechanical couplings, as would be understood by those of ordinary skill in the art. For example, a tightly fitting friction attachment, a spring-loaded detent feature, or matching ramped snap features on the pick head 110 and pick head interface 135 may be used to couple the pick head 110 to the interface 135. The installation and removal of the pick head 110 could be performed by a user manipulated mechanism that captures and/or releases the pick head 110, as described above. In the embodiment illustrated in FIG. 1D, the user-manipulated end of this mechanism is located at the bottom of the device 100.

The device 100 can be used in a variety of ways to improve oral hygiene. For example, the user may power on the device 100 to cause the pick head 110 to vibrate at the desired frequency, and the user may guide the tip of the pick member 111 and/or the pick head 110 over the surface of the user's teeth, including the regions between teeth, at the interface of the teeth and gums, and/or below the gum line. Biofilm is a sticky film that initially is easily removed with firm contact, but if given time to mineralize, is very difficult to remove. Therefore, it may be desirable for the user to perform cleaning sessions on a frequent basis, such as once or twice a day. The primary cleaning target is the junction between the gum and teeth. In some embodiments, a single pass over that junction with the pick head 110 and/or pick member 111 may be sufficient. In other embodiments, it may be desirable for the user to pass the pick head 110 and/or pick member 111 multiple times over each junction in order to ensure thorough cleaning. The device 100 may include a timer to provide the user with feedback to indicate that a predetermined length of time for the cleaning session has elapsed. For example, during use, the device 100 may issue an audible or tactile alert to indicate that the predetermined session length (e.g., two or three minutes) has elapsed. In some embodiments, the device 100 may be configured to automatically power off after the elapsed period of time. In some other examples, the timer may generate time data which indicates the duration of a particular cleaning session using device 100. This time data can be displayed to the user or transmitted to another computing device for analysis (e.g., to confirm the user's compliance with recommended durations of cleaning sessions).

As described above, the device 100 may include a digital camera for capturing images and/or video of the user's teeth and gums during cleaning sessions. These images and/or video may be stored in a memory provided in the device 100 and then transferred to other computing devices wirelessly using a wireless communications interface, e.g., a short-range communication protocol such as Bluetooth (depicted in FIG. 6A), near-field communication (NFC), or over a wireless local area network (LAN). This short-range wireless communications interface may utilize a low power transmission from the device 100 with a transmission range of, e.g., 1-10 cm up to 1-10 m. In other embodiments, the device 100 may include a communications interface, such as a USB port, for a wired connection with a computing device to transfer the images and/or video. In other embodiments, the device 100 may have a wireless communications module, including an antenna, radio, and communication logic for wireless communications with external devices, such as the user's smartphone. In yet other embodiments, the inductive charging link between the device 100 and the charging base 410 may also be used for digital communication between the device 100 and the base 410. The base 410 may then have a wired or wireless link to a local or remote computing device. For example, base 410 may include a Wi-Fi transmitter or Wi-Fi dedicated chip and an antenna. Any short or long range communications protocol may be used, depending on the desired functionality.

In some examples, image and/or video data may be transmitted to a display device, such as a mobile phone, smart mirror, tablet, computing device, augmented reality display, virtual reality display, or the like, in real time so that a user of device 100 may use the display device to monitor the position of the pick head 110 in the user or subject's mouth. In other examples, previously-stored video and/or images of previous cleaning sessions may be transferred to various display devices, such as those mentioned above, for reference, diagnosis, research, and/or treatment purposes.

In some examples, image data captured by image capture device 140 and any other user data may be stored by the control module of the device in memory until such time as device 100 is placed in charging base 410 or until power is being supplied to device 100. When power is being supplied to device 100, device 100 may transmit data stored in the device memory to a wireless internet enabled device. In an example, image capture device 140 may capture a plurality of images and/or videos of a user's mouth and/or teeth while the user is using device 100. The plurality of images and/or videos, hereinafter referred to as "image data", may be stored in the memory of device 100. Device 100 may transmit the image data using a short-range communication protocol when device 100 is supplied with power, such as, for example, when device 100 is placed in charging base 410. For example, device 100 may include a Bluetooth radio. Device 100 may transmit the image data to charging base 410 via Bluetooth when power is supplied to device 100. By eliminating the need to power wireless communications using battery power alone, the device 100 may utilize smaller-capacity batteries, thereby reducing cost and size of the device 100. Charging base 410 may be configured for wireless local area network communications (e.g., Wi-Fi enabled) and may transmit image data over the wireless LAN to another computing device on the wireless LAN or website or other computing device on a WAN. For example, image data may be transmitted to any number of healthcare professionals such as dental practitioners, dental professionals, dental assistants, medical professionals and/or assistants, researchers, archivists/analysts, etc. Advantageously, transmission of image data only when device 100 is supplied with power may provide for longer battery life of the device 100. In some embodiments, data may be transmitted by the device 100 automatically upon detection of a predetermined event (e.g., initiation of charging session indicating that the device 100 has been placed in charging base 410 or upon completion of the cleaning session). In some other examples, image data captured by image capture device 140 may be transmitted in real time or manually in response to a control command or "sync" command received as an input at an interface of device 100 or of a mobile application configured in communication with device 100. Additionally, image data need not be transmitted from device 100 to charging base 410. In some other examples, image data may be transmitted directly from device 100 to another computing device such as a smart phone, tablet computer, laptop, desktop, or other Wi-Fi enabled device. Additionally, in embodiments where device 100 includes a Wi-Fi transmitter and antenna, device 100 may transmit image data over a network to any number of healthcare professionals such as dental practitioners, dental professionals, dental assistants, medical professionals and/or assistants, researchers, archivists/analysts, etc.

In some embodiments, the memory in the device 100 may be used to store other information regarding the status or usage of the device 100. For example, the control module of the device 100 may be configured to store information regarding each cleaning session (e.g., time of day, duration of cleaning session, frequency of cleaning, etc.). This information may be transferred to a local or remote computing device along with the images and video, as described above. The control module may comprise a microcontroller (sometimes referred to herein as a "processor") which monitors the power button 122, controls the vibration element, controls the light source 144, controls and receives data from the image capture device 140, storage usage history, and communicates with external devices.

In some embodiments, the device 100 may include additional functionality. For example, the device 100 may include position or motion sensors, such as accelerometers, gyroscopes, or magnetometers. These position and/or motion sensors may be used to roughly track and generate position data related to the pick head's motion through the user's mouth to track proper use and position of the device 100. As described above, in some examples, the device 100 may include one or more markings on pick head 110. Markings on pick head 110 may be used in conjunction with image data from the image capture device 140 as well as data generated by the position and motion sensors to determine the position of pick head 110 in a coordinate space or to determine a reference location in the user's mouth. The device 100 may also include force feedback functionality. A pressure sensor may be positioned between the vibration element and housing to measure axial force on the pick head 100. The device 100 may alert the user using sound or vibration feedback to guide the user to use the proper force range.

In various examples, the device 100 may include one or more molecular sensors. For example, device 100 may include an optical sensor, a spectrophotometer, a spectrometer, or the like. The molecular sensor may be effective to identify proteins and/or other molecules present on a user or subject's teeth or in the gingival crevicular fluid (GCF). Certain molecules may be indicative of inflammation or pathogens related to periodontal disease found in the user's mouth. In some examples, a processor of device 100 may consider information from a force sensor of device 100 in conjunction with data received from the molecular sensor in order to determine if the relative proportions of molecules and/or proteins which are related to inflammatory response is due to insufficient or excessive force of the application of pick head 110 to the user's teeth. Data collected by a molecular sensor of device 100 may be stored in a memory and may be transmitted to dental professionals, dental practitioners, assistants, medical professionals or assistants, researchers, and/or archivists/analysts for analysis. For example, an abundance of certain proteins such as cytokines (IL-1β, TNFα), prostaglandins (PGE2), and immunoglobulins may indicate to the dental professional, dental practitioner, researcher and/or other analyst receiving the data, that the user is experiencing inflammation. In some other examples, various host derived enzymes may be of interest to researchers and dental professionals in order to study pathogenesis and/or progression and management of periodontal disease. Some example host derived enzymes include alkaline phosphatase, aspartate aminotransferase, and matrix metalloproteinases. Additionally, tissue breakdown products may be identified with a sensor, sampled, and/or studied. Some example tissue breakdown products include glycosaminoglycans and laminin.

In some examples, the device 100 may include a pH sensor in pick head 110 and/or pick member 111. The pH sensor may be effective to determine localized pH on particular teeth and/or within particular caries, pockets, and/or furcations of particular teeth. Some periodontal pathogens thrive within environments of a certain range of pH. For example, a particular periodontopathogen in the biofilm may favor pH levels between 6-8. If the pH sensor of pick head 110 and/or pick member 111 determines that the pH of a particular pocket or furcation is within the pH range 6-8, device 100 or a processor of device 100 may generate an alert to the user. Audible, tactile, and/or visible alerts may be generated, in various examples, and as described previously herein. The alert may be produced directly by device 100 (such as, for example, a pH readout on a display of device 100) or by an application associated with device 100. For example, a user's smartphone may receive pH information from device 100 and may alert the user through a software application associated with device 100 that the pH is favorable to pathogenic organisms. In some further examples, the alert may further suggest that the user adjust the pH of the localized region. For example, a user may apply a treatment to pick head 110 to adjust the pH of the localized region to a pH which is not favorable for pathogens of concern. In another example, device 100 may include a pH adjustment buffer which may be automatically dispersed by pick head 110/pick member 111 or which may impregnate pick head 110/pick member 111 when a certain pH or pH range is detected by the pH sensor. For example, if the pH sensor detects a pH within the range of 6-8 within a particular pocket on a user's tooth, a processor of device 100 may activate a pump or pressurized reservoir of an alkaline solution to coat pick head 110 with the alkaline solution. The pH of the particular pocket may thereby be adjusted by application of the alkaline solution to the pocket. The user may be alerted by device 100 when the pH has reached an acceptable range. Some examples of pH treatment solutions may include sodium bicarbonate ($NaHCO_3$), potassium bicarbonate ($KHCO_3$), or a magnesium salt, such as $MgCl_2$, for example. Such pH treatments may be more effective than mouth rinses or other similar treatments due to the mechanical action of pick head 110/pick member 111. Unlike with rinses, the mechanical action provided by pick head 110/pick member 111 may allow the pH treatment to reach beneath the surface of sticky biofilm deposits and beneath the gum surface.

FIGS. 5A-5D illustrate various screen shots of a software application that may be used in conjunction with the device 100. This software application may be an application executing on a portable computing device, such as a smartphone or tablet computer, or on a laptop or desktop personal computer.

Figure 5A:
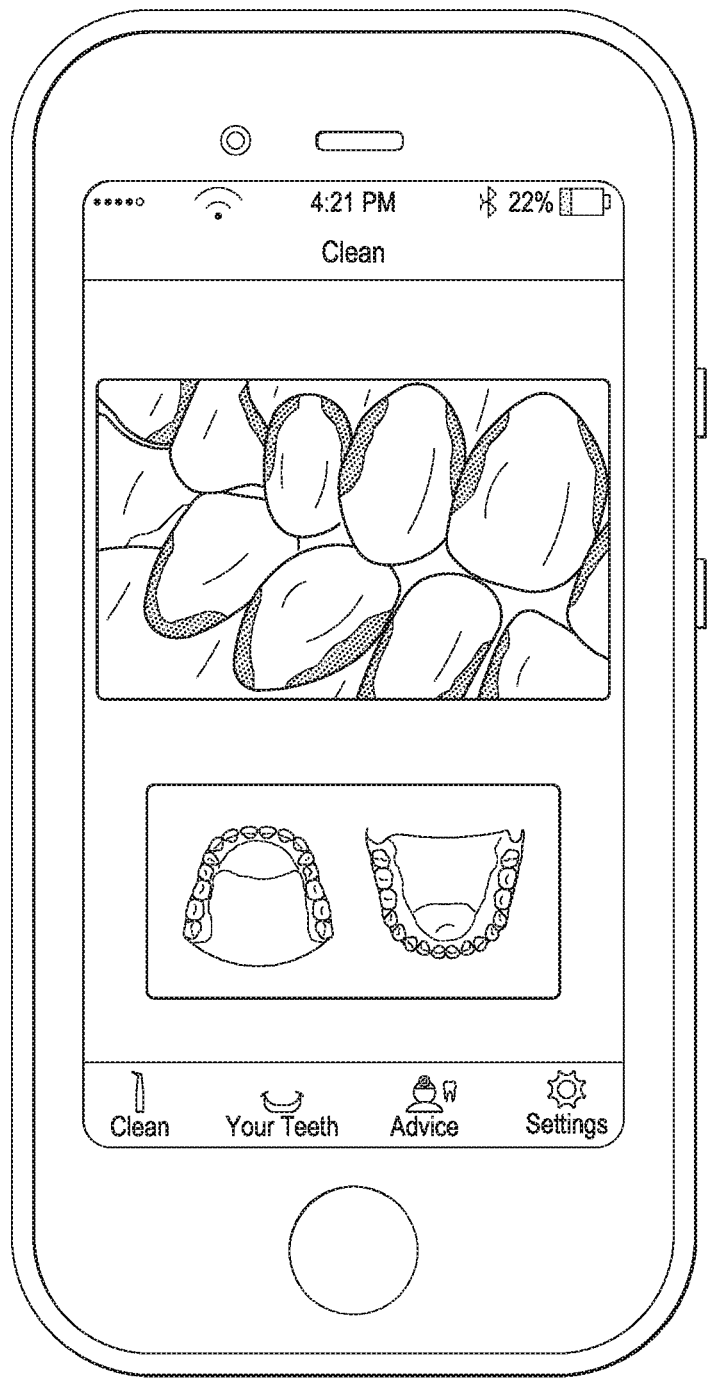
FIG. 5A illustrates an instructional or coaching module of a software application for use in conjunction with an oral hygiene device, in accordance with various aspects of the present disclosure.

FIG. 5A illustrates an instructional or coaching module of the software application. The coaching module may provide basic instructions on how to operate the device 100, and may also provide feedback to the user of any regions of the user's mouth which were missed in previous cleaning sessions. The coaching module may illustrate a path tracing where the user should guide the pick head during cleaning sessions. This feedback may be based on analysis of the user data, including previously-recorded images, positional data, time data, and/or video from previous sessions by the user's local computing device or by a remote server. In some examples, the coaching module may be implemented in an augmented reality (AR) or virtual reality (VR) module. For example, a user may see a virtual 3D model of the user's teeth through an AR or VR display along with a representation of device 100. The position of the representation of device 100 in the AR/VR display with respect to the virtual 3D model of the user's teeth may correspond to the position of device 100 with respect to user's teeth. Accordingly, the AR/VR display may help the user to guide device 100 over the user's teeth. In some examples, healthcare professionals such as dental practitioners, dental professionals, dental assistants, medical professionals and/or assistants, researchers, archivists/analysts, etc. may provide indicators to the AR/VR module. Indicators may emphasize problem areas where a user may want to focus their cleaning efforts with device 100. For example, a tooth with a particularly deep pocket may be colored red or blue so that the user knows to focus their efforts on the particular tooth. In another example, the representations of teeth in the AR/VR display may change colors after being cleaned with device 100, so that a user knows that he has already cleaned a particular tooth. In some other examples, dental professionals, assistants, dental practitioners, medical professionals or assistants, researchers, and/or archivists/analysts may provide real time or pre-recorded instructions to a user. Such instructions may be related to the particular dental history of the user and/or to the particular techniques of an on-going cleaning session.

Figure 5B:
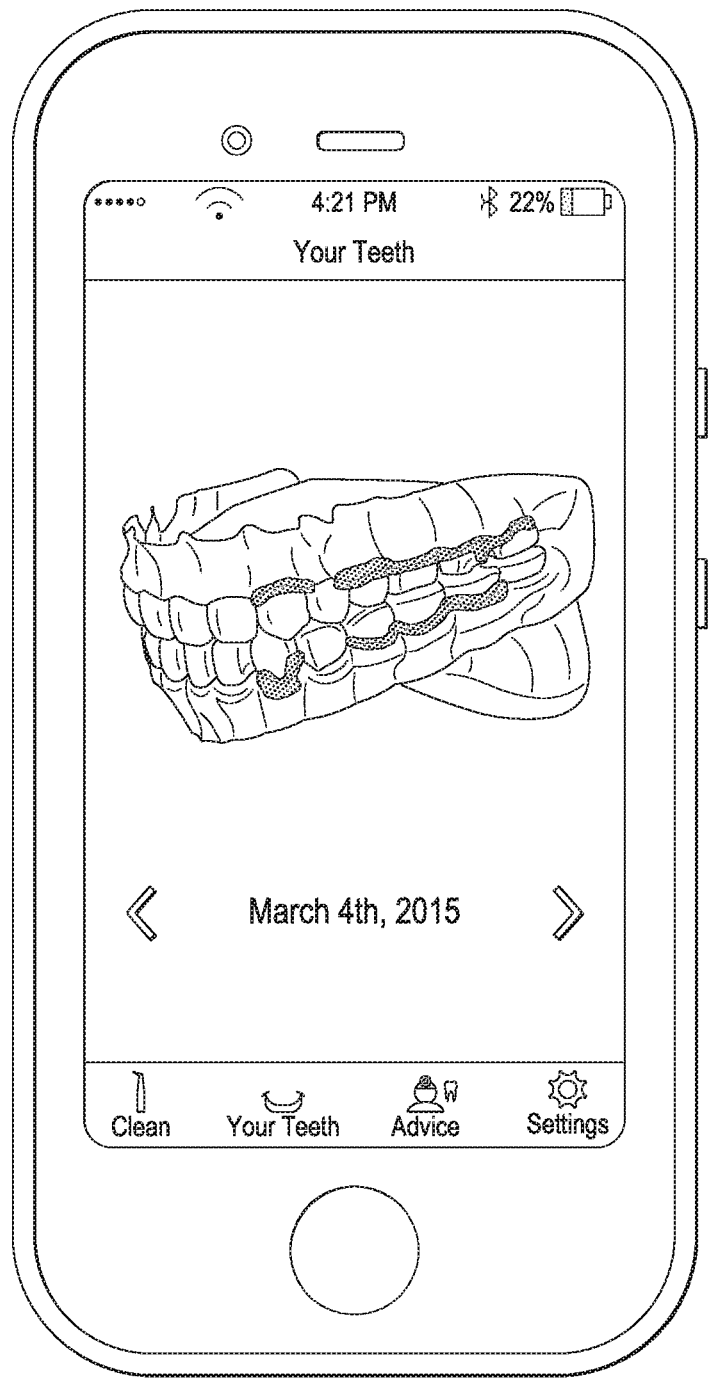
FIG. 5B illustrates a 3D model of a user's teeth highlighting problem areas, in accordance with various aspects of the present disclosure.

FIG. 5B illustrates a 3D model of the user's teeth highlighting problem areas. These areas may be identified by the user's healthcare provider based on the provider's in person examination of the user, or may be identified based on analysis of the images and/or video captured by the device 100. In some examples, image capture device 140 may be effective to take a plurality of images of a user's mouth in order to construct a 3D model of the user's mouth. In some examples, the construction of the 3D model of the user's mouth may be performed by a processing unit integrated into device 100. In other examples, the image data captured by image capture device 140 may be transmitted to another device, as described above, where an application may be effective to construct the 3D model of the user's teeth and/or mouth. Various sensors on device 100 such as gyroscopes, accelerometers, transducers to detect force or pressure of pick head 110 and/or pick member 111, and/or image capture device 140 may be effective to generate data related to a position of pick head 110 in a user's mouth. In various examples, a processor of device 100 or configured in communication with device 100 may use position data generated by such sensors and/or image data generated by image capture device 140 to determine a reference point in the user's mouth, a 3D model of the user's mouth, and/or a position of pick head 110 in the user's mouth. For example, pick head 110 may have various markings of known distance from a lens of image capture device 140. Various distances of pockets in teeth and space between teeth from the lens of image capture device 140 may be determined by interpolating between known distances, such as by using the markings of pick head 110 as reference points or by using a reference point in the mouth determined using a combination of sensors of device 100. In various examples, a difference between the surface area of a 3D model generated before a cleaning session and the surface area of a 3D model generated after such a cleaning session may be determined. The difference in surface area may represent an amount of biofilm and/or food particles removed from the user's teeth during the cleaning session. Such information may be stored in a memory either on device 100 or on the device calculating the change in surface area. The difference in surface area may be described and/or displayed in terms of a percentage reduction of biofilm or plaque to provide feedback to a user of device 100.

In some examples, a 3D model of the user's mouth may be created by specialized image equipment at the office of dental professionals, assistants, dental practitioners, medical professionals or assistants, researchers, and/or archivists/analysts, or at another specialized facility for creating 3D models. The 3D model may be accessible by a smartphone application which is, in turn, configured to communicate with device 100 including image capture device 140. Position data may be generated which is indicative of where in the 3D model of the mouth the user is using device 100 based on sensors in device 100 such as a gyroscope and accelerometer, for example, as well as image data provided by image capture device 140. Such position data may be provided to the user's dental professionals, assistants, dental practitioners, medical professionals or assistants, researchers, and/or archivists/analysts, for evaluation of the efficacy of one or more cleaning sessions. In this way, the dental professional, or other qualified individual, may be apprised of whether or not the user is correctly using the device 100 to clean the user's teeth and/or mouth.

In some examples, dental professionals, assistants, dental practitioners, medical professionals or assistants, researchers, and/or archivists/analysts may be aware of one or more "problem areas" in a user's mouth. For example, a user may have a particularly deep pocket or furcation on a particular tooth which may be difficult to clean. In another example, the underside of a crown of an implanted tooth may be a problem area. In some examples, dental professionals, assistants, dental practitioners, medical professionals or assistants, researchers, and/or archivists/analysts may be aware of such problem areas by virtue of an in-person examination of the particular user. In other examples, a user may send images of the user's teeth captured by image capture device 140 and/or a 3D representation of the user's teeth (generated, for example, by a processor of device 100 based on image data captured by image capture device 100) to the dental professionals, assistants, dental practitioners, medical professionals or assistants, researchers, and/or archivists/analysts. The dental professionals, assistants, dental practitioners, medical professionals or assistants, researchers, and/or archivists/analysts may identify problem areas based on the image data and/or the 3D representations received from device 100. The dental professionals, assistants, dental practitioners, medical professionals or assistants, researchers, and/or archivists/analysts may sync such problem area information with device 100 or with an application related to device 100. Thereafter, during a cleaning session, when pick head 110 is determined to be proximal to a previously-defined problem area, device 100 may provide an indicator so that the user of device 100 may be aware that they are approaching a problem area. Device 100 may determine that pick head 110 is proximal to a problem area based on, for example, various position sensors of device 100 (described in further detail above), image data generated by image capture device 140, a 3D model of the user's mouth, or some combination thereof. An indicator may comprise, for example, an audible cue, such as a bell, chime, tone, or verbal information such as spoken instructions or descriptions of the problem area. In other examples, the indicator may include a visible cue such as a light, on-screen instructions, and/or an on-screen display of the position of pick head 110 and of a representation of the user's mouth including the problem area. In examples where the problem area is displayed on a visual display to the user, the problem area may be highlighted so that the user is able to focus their cleaning efforts on the problem area. In some other examples, the indicator may be a tactile clue such as a vibration or pattern of vibration.

Figure 5C:
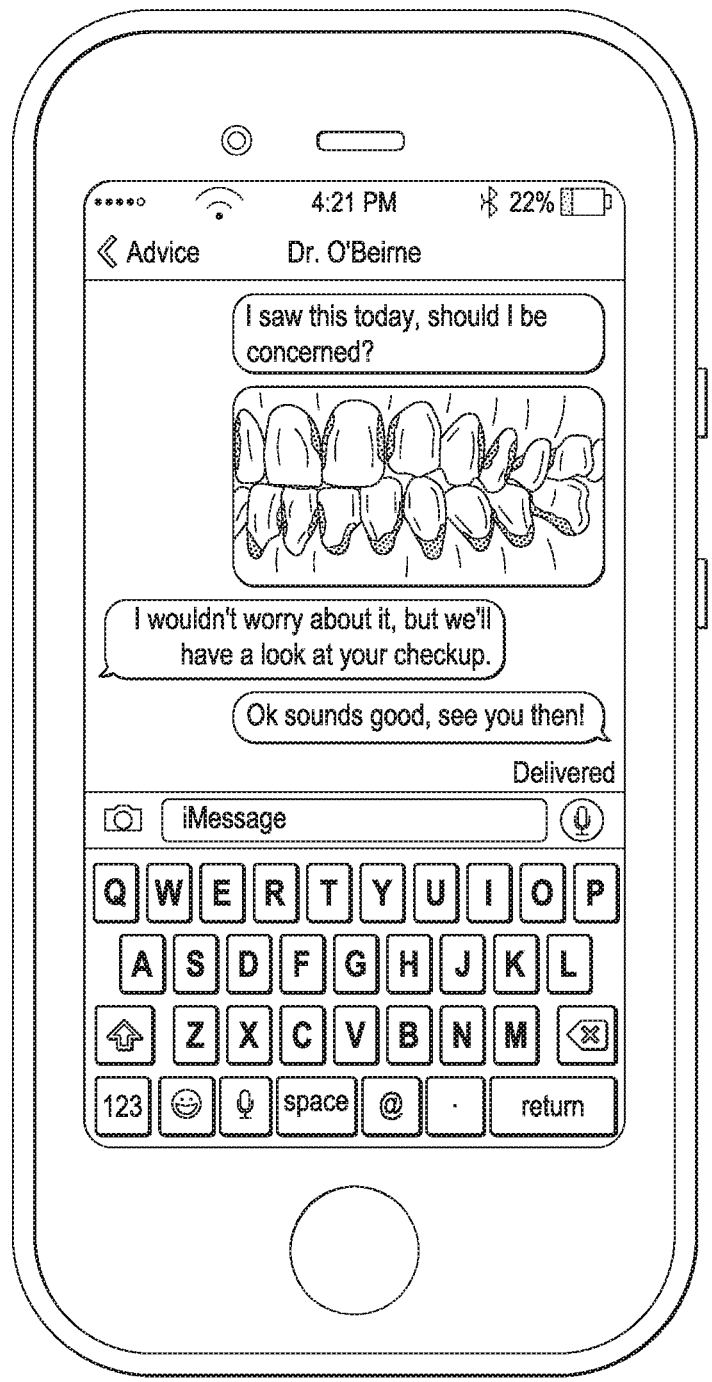
FIG. 5C illustrates a communication module of a software application, in accordance with various aspects of the present disclosure.

FIG. 5C illustrates a communication module of the software application. This communication module may enable direct communication between the user and the user's healthcare provider, such as a dentist, dental practitioner, periodontist, medical professional or assistants of the aforementioned parties. In other examples, the communication module may enable communication between the user and a researcher, archivist, or laboratory analyst. The communication module may also include the capability of sharing images and video during the communication session.

Figure 5D:
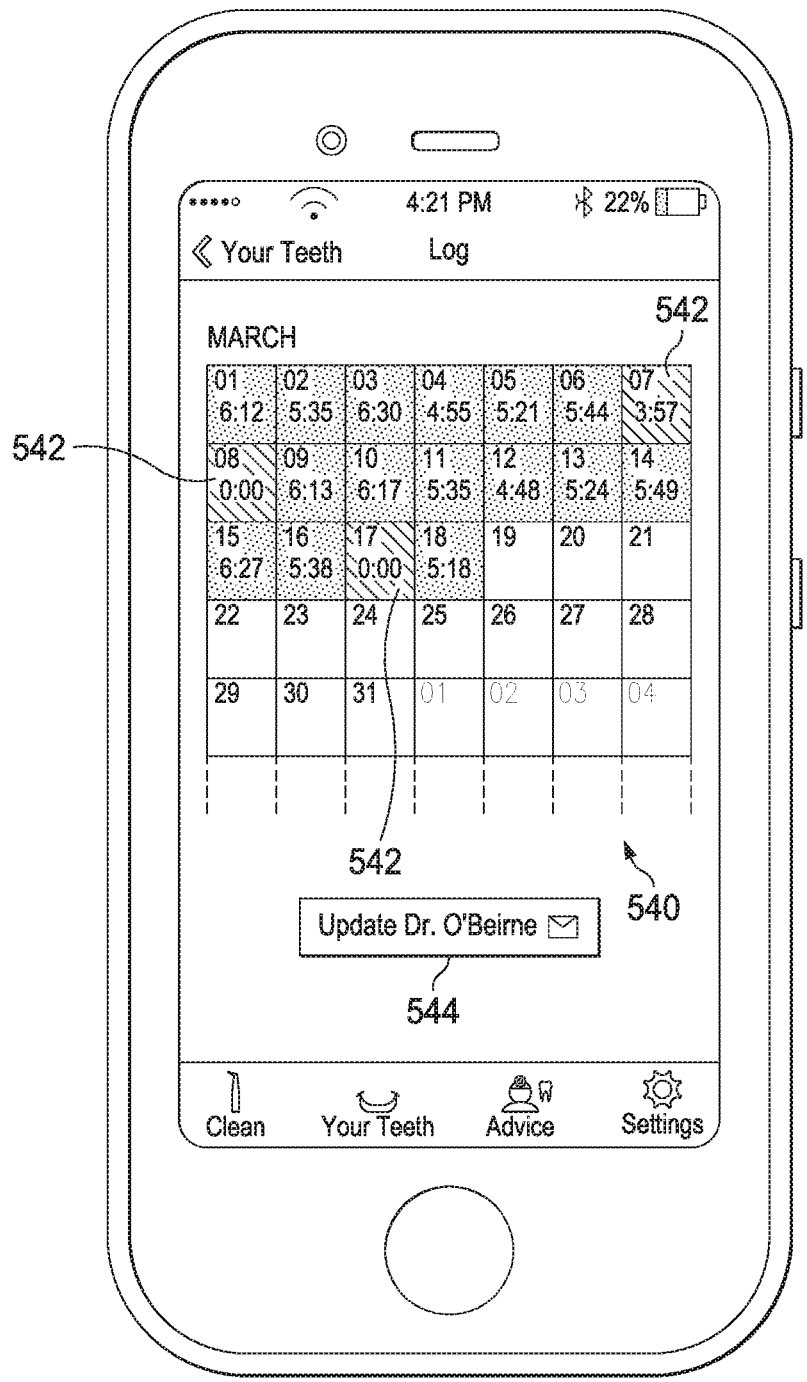
FIG. 5D illustrates a usage log module of a software application, in accordance with various aspects of the present disclosure.

FIG. 5D illustrates a usage log module of the software application. This usage log module may include a calendar portion 540 which can display various types of information regarding the user's operation of the device 100. In the illustrated example, the calendar portion 540 displays the total time spent operating the device 100 each day. The calendar portion 540 may also provide an alert or other indication of deviance from the targeted usage. In the illustrated embodiment, the days 542 during which the total time spent using the device was below a threshold target time (e.g., 4 minutes) are shown in a different color to emphasize the deviation. The usage log module may also include an input control (e.g., button 544), which, when selected by the user, causes the software application to transmit the storage usage log information to the user's health care provider. The software can accomplish this by causing the computing device to launch an email message to the health care provider's email address containing the usage log information (e.g., as an attachment file to the email).

While the invention has been described in terms of particular embodiments and illustrative figures, those of ordinary skill in the art will recognize that the invention is not limited to the embodiments or figures described. For example, in various embodiments described above, the device is used for cleaning between the teeth and gums and within pockets and/or furcations in the mouth of a user or subject. In other embodiments, the device may be used to sample biofilm removed from the patient's mouth during cleaning sessions. In some embodiments, a dedicated biofilm sample head is used with the device 100 to gather biofilm samples and/or gingival crevicular fluid from the user's mouth. In other embodiments, the pick head 110 used for cleaning sessions is used, since the biofilm will naturally be collected on the surface of the pick head 110 during a cleaning session. The user may then remove the pick head 110 and place it in a sterile container or packaging for sealing the pick head 110 for transfer to the user's health care provider and/or to a laboratory for analysis. In some embodiments, the packaging may be configured to assist with the detaching of the pick head 110 from the device to prevent the user's hands from contacting the pick head 110 and removing or contaminating the biofilm sample collected thereon. For example, the packaging may include a flexible portion that can receive the pick head 110 inside the packaging and be gripped by the user on the outside of the packaging to facilitate the detaching of the pick head 110 from the device 100. In other embodiments, the device 100 may include a removal actuation mechanism coupled to the eject button 152 to eject the pick head 110 from the device 100 after use without requiring the user to manually grasp the pick head 110.

The device 100 may be used by humans or be used in veterinary applications to clean the teeth and gums of animals, such as dogs, cats, or other pets.

In some embodiments, the pick head 110 may be coated with a therapeutic or flavor-enhancing substance. For example, the pick head 110 may be coated with a sugar alcohol such as xylitol, which can provide beneficial anti-cariogenic effects as well as provide a pleasant taste. In some embodiments, an antiseptic and/or antibacterial substance may be coated on the pick head 110. In yet other embodiments, a probiotic material may be coated on the pick head 110 to introduce beneficial bacteria into the user's mouth.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

Specific elements of any embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. An oral hygiene system, comprising:
a handle portion;
a head portion coupled to the handle portion, the head portion including a pick head interface;
a pick head removably coupled to the pick head interface, the pick head comprising a pointed pick member comprising a core and an outer region surrounding the core, the outer region comprising a porous and pliable material softer than dentin of human teeth and suitable for removing biofilm from between teeth and gums, wherein a first hardness of the core is greater than a second hardness of the outer region; and
a vibration element coupled to the pick head via the pick head interface, the vibration element configured to vibrate the pick head during a cleaning session.

2. The system of claim 1, wherein the pick head is impregnated with a treatment effective to enhance biofilm removal.

3. The system of claim 1, wherein:
the vibration element is configured to vibrate the pick head at a frequency of about 20 Hz to about 1,000 Hz.

4. The system of claim 1, further comprising a molecular sensor effective to identify one or more molecules indicative of inflammation.

5. The system of claim 1, further comprising an image capture device disposed in the head portion, the image capture device effective to capture image data representing images of an area proximal to a tip of the pointed pick member.

6. The system of claim 1, wherein the pick head is impregnated or coated with probiotics for promoting growth and cultivation of a desired biome.

7. The system of claim 5, further comprising:
a memory effective to store image data captured by the image capture device; and
a short-range communications interface configured to transmit image data captured by the image capture device to a second device.

8. The system of claim 5, further comprising:
at least one sensor selected from a group comprising an accelerometer, a gyroscope, and a magnetometer;
wherein the at least one sensor is effective to generate position data related to one or more positions of the pick head during the cleaning session.

9. The system of claim 8, further comprising:
a processor; and
a memory;
the processor effective to:
store the image data captured by the image capture device in the memory;
store the position data in the memory;
determine the one or more positions of the pick head during the cleaning session based at least in part on the image data and the position data;
store the one or more positions in the memory; and
store cleaning session data indicating cleaning session duration and frequency of cleaning.

10. The system of claim 9, further comprising:
a short-range communication device effective to transmit the one or more positions, the position data, the cleaning session data, and the image data to a second device while the oral hygiene system is being supplied with power.

11. The system of claim 10, wherein the second device is effective to:
    receive the one or more positions, the position data, the cleaning session data, and the image data; and
    evaluate the cleaning session based at least in part on one or more of the position data, the image data, the cleaning session data, or the one or more positions.

12. The oral hygiene system of claim 5, further comprising:
    a handset comprising:
        the handle portion;
        the head portion;
        the pick head;
        the image capture device;
        a short-range communications interface; and
        a battery electrically coupled to the image capture device and the short-range communications interface; and
    a charging base sized and shaped so as to couple to the handset, the charging base comprising:
        an inductive charging link effective to supply power to the battery when the handset is coupled to the charging base;
        a Wi-Fi transmitter; and
        an antenna effective to be in communication with the Wi-Fi transmitter;
    wherein the short-range communications interface is effective to transmit the image data to the Wi-Fi transmitter of the charging base.

13. The system of claim 12, wherein the short-range communications interface is configured to transmit the image data to the Wi-Fi transmitter of the charging base when the inductive charging link is supplying power to the battery.

14. The system of claim 12, the charging base further comprising a compartment effective to store one or more replacement pick heads.

15. The system of claim 14, the charging base further comprising a sensor in the compartment effective to determine that fewer than a number of the one or more replacement pick heads remain in the compartment.

16. The system of claim 12, the handset further comprising:
    at least one sensor selected from a group comprising an accelerometer, a gyroscope, and a magnetometer;
    wherein the at least one sensor is effective to generate position data related to one or more positions of the pick head.

17. The system of claim 12, further comprising a polisher cup pick head adapted to couple with the pick head interface.

18. The system of claim 5, further comprising a light source configured to illuminate an area to be captured by the image capture device.

19. The system of claim 1, further comprising a pressure sensor effective to measure axial force on the pick head.

20. The system of claim 1, wherein the pick head comprises textured features configured to collect samples of biofilm from a user's teeth during operation of the oral hygiene system.

21. The system of claim 1, further comprising a sterile container sized to contain the pick head.

22. The system of claim 1, further comprising a sensor configured to determine localized pH in a user's mouth or a molecular sensor configured to identify molecules present in the user's mouth indicative of inflammation or pathogens related to periodontal disease.

23. The system of claim 1, wherein the pointed pick member comprises wood or a cellulose material.

24. The system of claim 1, wherein the pointed pick member comprises a material softer than 3 Mohs on the Mohs hardness scale.

25. The system of claim 1, wherein the pick head is impregnated with a treatment effective to enhance biofilm management, the treatment comprising one or more of: probiotics for promoting growth and cultivation of a desired biome; molecules effective to block bacterial functions; antibodies that block a surface antigen; an enzyme treatment to slow or prevent bacterial attachment; non-pathogenic organisms to slow or prevent attachment and proliferation of pathogenic biofilms; or molecules effective to down-regulate an inflammatory response in teeth or gums.

26. The system of claim 1, wherein the pick head is configured to collect samples of biofilm and gingival crevicular fluid during operation of the oral hygiene system.

27. The system of claim 1, wherein the pick head is impregnated or coated with one or more of: hydrogen peroxide, xylitol, fluoride, ginger, pineapple, cranberry, sodium hypochlorite, sodium chlorate, chlorine dioxide, chlorhexidine, essential oils, spearmint oil, or tea tree oil.

28. The system of claim 1, further comprising a molecular sensor effective to identify one or more molecules present on a user's teeth or in the user's gingival crevicular fluid (GCF).

29. The system of claim 1, wherein:
    the handle portion extends along a long axis; and
    the pick head extends away from the head portion at an angle non-parallel with the long axis of the handle portion.

30. An oral hygiene system, comprising:
    a handle portion;
    a head portion coupled to the handle portion, the head portion including a pick head interface;
    a pick head removably coupled to the pick head interface, the pick head comprising a pointed pick member comprising a core and an outer region surrounding the core, the outer region comprising a porous and pliable material softer than dentin of human teeth and suitable for removing biofilm from between teeth and gums, wherein a first hardness of the core is greater than a second hardness of the outer region;
    a light source configured to illuminate a user's mouth; and
    a vibration element coupled to the pick head via the pick head interface, the vibration element configured to vibrate the pick head during a cleaning session.

31. The system of claim 30, wherein the pick head is configured to collect samples of biofilm and gingival crevicular fluid during operation of the oral hygiene system.

32. The system of claim 30, wherein:
    the handle portion extends along a long axis; and
    the pick head extends away from the head portion at an angle non-parallel with the long axis of the handle portion.

* * * * *